(12) United States Patent
Tanaka et al.

(10) Patent No.: US 12,023,429 B2
(45) Date of Patent: Jul. 2, 2024

(54) PHOTODYNAMIC THERAPY DEVICE AND PHOTODYNAMIC THERAPY DEVICE CARTRIDGE

(71) Applicant: OTSUKA ELECTRONICS CO., LTD., Hirakata (JP)

(72) Inventors: Akira Tanaka, Hirakata (JP); Shinpei Kajiwara, Hirakata (JP)

(73) Assignee: OTSUKA ELECTRONICS CO., LTD., Hirakata (JP)

(*) Notice: Subject to any disclaimer, the term of this patent is extended or adjusted under 35 U.S.C. 154(b) by 460 days.

(21) Appl. No.: 17/433,864

(22) PCT Filed: Feb. 26, 2019

(86) PCT No.: PCT/JP2019/007378
§ 371 (c)(1),
(2) Date: Aug. 25, 2021

(87) PCT Pub. No.: WO2020/174589
PCT Pub. Date: Sep. 3, 2020

(65) Prior Publication Data
US 2022/0133976 A1 May 5, 2022

(30) Foreign Application Priority Data
Feb. 25, 2019 (WO) .................. PCT/JP2019/007128

(51) Int. Cl.
*A61M 1/36* (2006.01)
*A61N 5/06* (2006.01)

(52) U.S. Cl.
CPC .......... *A61M 1/3683* (2014.02); *A61N 5/062* (2013.01); *A61M 2205/18* (2013.01); *A61N 2005/0628* (2013.01); *A61N 2005/0652* (2013.01)

(58) Field of Classification Search
CPC .............. A61M 1/3683; A61M 1/3681; A61M 1/3621; A61M 1/36; A61M 2205/18;
(Continued)

(56) References Cited

U.S. PATENT DOCUMENTS 5,702,432 A 12/1997 Chen et al.
5,707,594 A 1/1998 Austin
(Continued)

FOREIGN PATENT DOCUMENTS

CN 102068723 A 5/2011
CN 106461780 A 2/2017
(Continued)

OTHER PUBLICATIONS

Extended European Search Report dated Sep. 9, 2022, in corresponding European Patent Application No. 19916662.0, 5 pages.
(Continued)

*Primary Examiner* — Scott M. Getzow
(74) *Attorney, Agent, or Firm* — Oblon, McClelland, Maier & Neustadt, L.L.P.

(57) ABSTRACT

Provided is a photodynamic therapy device that enables efficient light irradiation of blood of a patient. A photodynamic therapy device (100) of this disclosure includes a cartridge (10) including a winding core and a tube arranged so as to be wound around the winding core, a casing (50) configured to accommodate the cartridge (10), and a light source (60), which is arranged inside the casing (50), and is configured to irradiate the tube with light. The tube arranged around the winding core has a cross section taken along a direction orthogonal to an extending direction of the tube, which has a first dimension in a first direction and a second dimension in a second direction orthogonal to the first
(Continued)

direction. The second dimension is smaller than the first dimension. The second direction is directed outward with respect to the winding core.

20 Claims, 8 Drawing Sheets

(58) Field of Classification Search
CPC .............. A61M 1/36226; A61N 5/062; A61N 2005/0628; A61N 2005/0652
See application file for complete search history.

(56) References Cited

U.S. PATENT DOCUMENTS

| 7,025,877 | B1 | 4/2006 | De Gheldere et al. |
| 2003/0030011 | A1 | 2/2003 | Brown et al. |
| 2003/0060747 | A1 | 3/2003 | Fries et al. |
| 2003/0064001 | A1 | 4/2003 | Fries et al. |
| 2003/0085173 | A1 | 5/2003 | DeGheldere et al. |
| 2003/0147770 | A1 | 8/2003 | Brown et al. |
| 2006/0197031 | A1 | 9/2006 | De Gheldere et al. |
| 2012/0116373 | A1 | 5/2012 | Moench et al. |
| 2013/0304019 | A1 | 11/2013 | Cooper et al. |
| 2016/0270851 | A1 | 9/2016 | Moench et al. |
| 2017/0312537 | A1 | 11/2017 | Mori et al. |

FOREIGN PATENT DOCUMENTS

| CN | 108434562 A | 8/2018 |
| JP | 2000-503579 A | 3/2000 |
| JP | 2003-501175 A | 1/2003 |
| JP | 2003-187482 A | 7/2003 |
| JP | 2004-533318 A | 11/2004 |
| JP | 2008-008849 A | 1/2008 |
| JP | 2012-533386 A | 12/2012 |
| JP | 2013-158717 A | 8/2013 |
| JP | 2018-65058 A | 4/2018 |
| WO | WO 00/74731 A1 | 12/2000 |
| WO | WO 2004/033081 A2 | 4/2004 |
| WO | WO 2011/090885 A2 | 7/2011 |
| WO | WO 2014/204001 A1 | 12/2014 |
| WO | WO 2015/162279 A1 | 10/2015 |
| WO | WO 2018/203495 A1 | 11/2018 |

OTHER PUBLICATIONS

Extended European Search Report dated Oct. 20, 2022 in European Patent Application No. 19917197.6, 5 pages.
International Search Report dated May 28, 2019 in PCT/JP2019/007378 filed on Feb. 26, 2019, 1 page.
Office Action issued Jan. 20, 2024, in Chinese Patent Application No. 201980092950.2, w/Partial Translation, citing document Nos. 15-18.

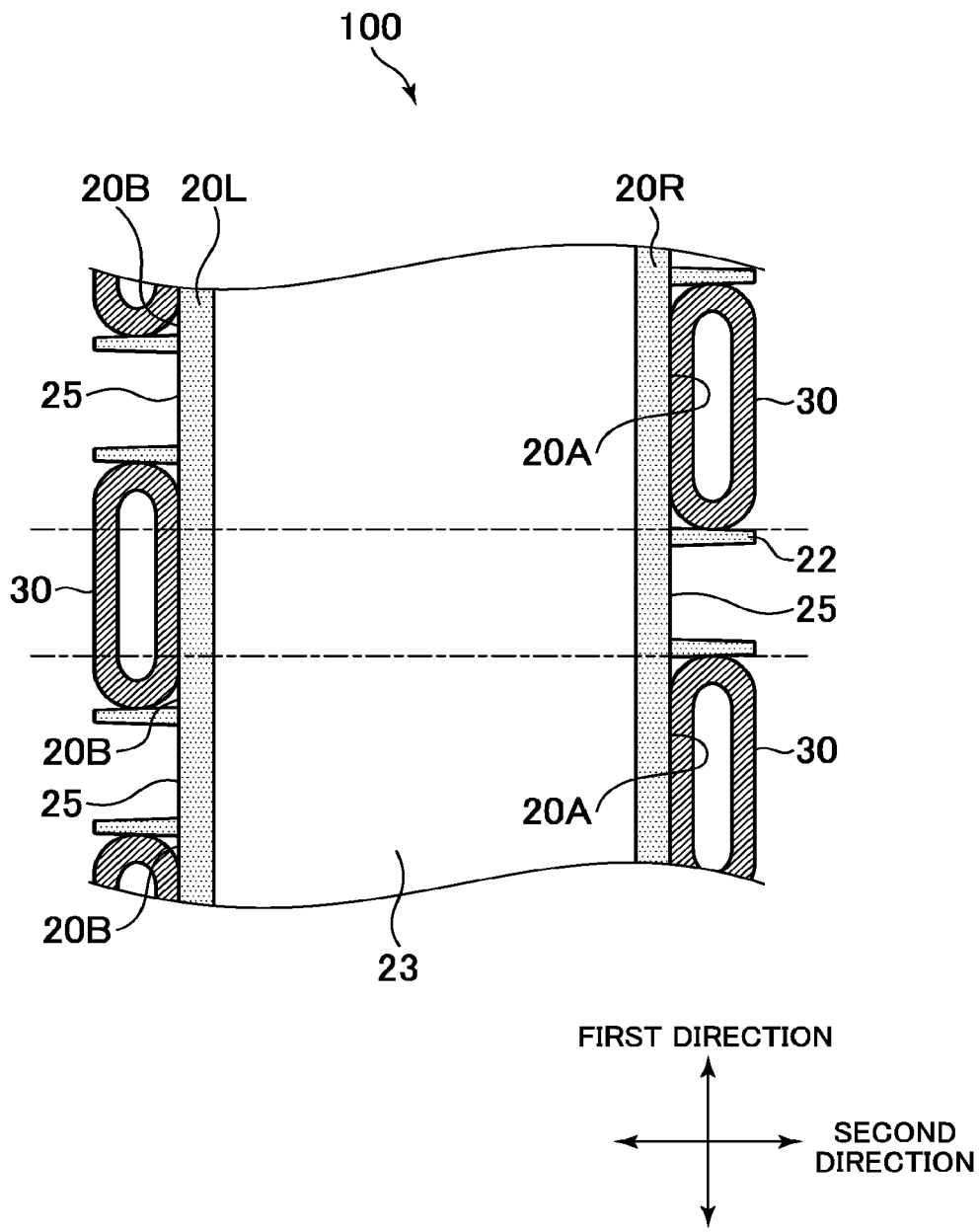

PHOTODYNAMIC THERAPY DEVICE AND PHOTODYNAMIC THERAPY DEVICE CARTRIDGE

TECHNICAL FIELD

The present invention relates to a photodynamic therapy device and a photodynamic therapy device cartridge.

BACKGROUND ART

In Patent Literature 1 described below, there is disclosed a photodynamic therapy device including a light bar and tubing. The light bar extends linearly, and accommodates a plurality of LEDs and a lead. The tubing is wound around the light bar, and is coupled to a circulatory system of a patient. Blood of the patient flows through the tubing, and is irradiated with light emitted from the LEDs. A photosensitizer is absorbed in the blood, and an undesirable component in the blood can be destroyed or affected through light irradiation from the LEDs.

CITATION LIST

Patent Literature

[PTL 1] JP 2000-503579 A

SUMMARY OF INVENTION

Technical Problem

In the related-art photodynamic therapy device, the blood flows through a flow path having a circular cross section, which is formed of the tubing, and is irradiated with light emitted from the LEDs to one side of the tubing. However, such a configuration has a problem in that efficient light irradiation of blood may not be achieved.

This disclosure has been made in view of the circumstances described above, and has an object to provide a photodynamic therapy device and a photodynamic therapy cartridge that enable efficient light irradiation of blood of a patient.

Solution to Problem

In order to solve the problems described above, according to this disclosure, there is provided a photodynamic therapy device, including: a cartridge including: a winding core; and a tube arranged so as to be wound around the winding core; a casing configured to accommodate the cartridge; and a light source, which is arranged inside the casing, and is configured to irradiate the tube with light, wherein the tube arranged around the winding core has a cross section taken along a direction orthogonal to an extending direction of the tube, which has a first dimension in a first direction and a second dimension in a second direction orthogonal to the first direction, the second dimension being smaller than the first dimension, and the second direction is directed outward with respect to the winding core.

BRIEF DESCRIPTION OF DRAWINGS

FIG. 8 is a sectional view for illustrating a photodynamic therapy device according to a modification example of the embodiment.

DESCRIPTION OF EMBODIMENT

An embodiment of this disclosure is described below with reference to the drawings.

Figure 1:
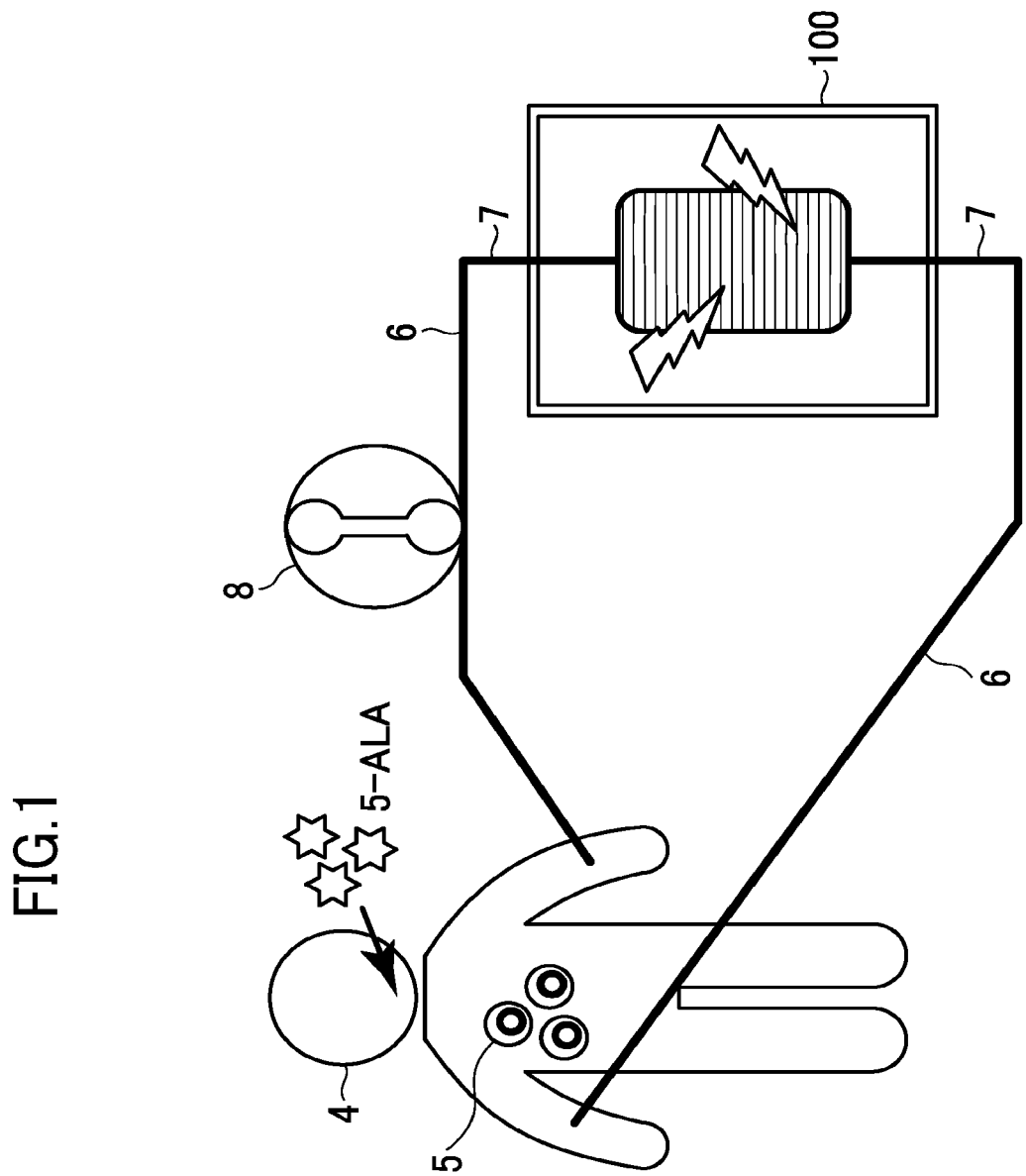
FIG. 1 is a schematic diagram for illustrating an outline of a photodynamic therapy according to an embodiment of this disclosure.

FIG. 1 is a schematic diagram for illustrating an outline of a photodynamic therapy according to this embodiment. In an example illustrated in FIG. 1, a patient 4 is a blood cancer patient, and has tumor cells 5. After 5-aminolevulinic acid (5-ALA) having oral absorbability is administered to the patient 4, 5-aminolevulinic acid is metabolized into protoporphyrin IX (PpIX), which is a photosensitive substance, in a biosynthetic process of heme in intercellular mitochondria. Protoporphyrin IX has a characteristic of accumulating in mitochondria in a tumor cell-specific manner, and thus accumulates in the tumor cells 5 of the patient 4.

Circulatory organs of the patient 4 are connected to a photodynamic therapy device 100 according to this embodiment via a blood circuit 6 and an irradiation blood circuit 7. Blood of the patient 4 contains the tumor cells 5 in which protoporphyrin IX has accumulated. The blood is caused to flow into the photodynamic therapy device 100 according to this disclosure via the blood circuit 6 and the irradiation blood circuit 7 by an action of an extracorporeal circulation pump 8 connected to the blood circuit 6. When the blood is irradiated with light having a wavelength falling within a wavelength range absorbable in protoporphyrin IX (for example, about 410 nm and in a range of from about 500 nm to 650 nm) in the photodynamic therapy device 100, protoporphyrin IX contained in the blood is brought into an excited singlet state. Protoporphyrin IX returns from the excited singlet state to a ground state through an excited triplet state. Oxygen, which has absorbed energy generated through the above-mentioned process, produces singlet oxygen that can destroy or affect the tumor cells 5 in the blood.

The blood irradiated with the light is returned to the circulatory organs of the patient 4 via the irradiation blood circuit 7 and the blood circuit 6 by an action of the extracorporeal circulation pump 8.

In the example described above, protoporphyrin IX is used as an example of the photosensitive substance. However, the photosensitive substance according to this disclosure is not limited to protoporphyrin IX. Further, in the example described above, the patient 4 is a blood cancer patient and has the tumor cells 5. However, a target according to this disclosure is not limited to the tumor cells 5. Any undesirable component in blood, in which the photosensitive substance accumulates, may be the target according to this disclosure.

Figure 2:
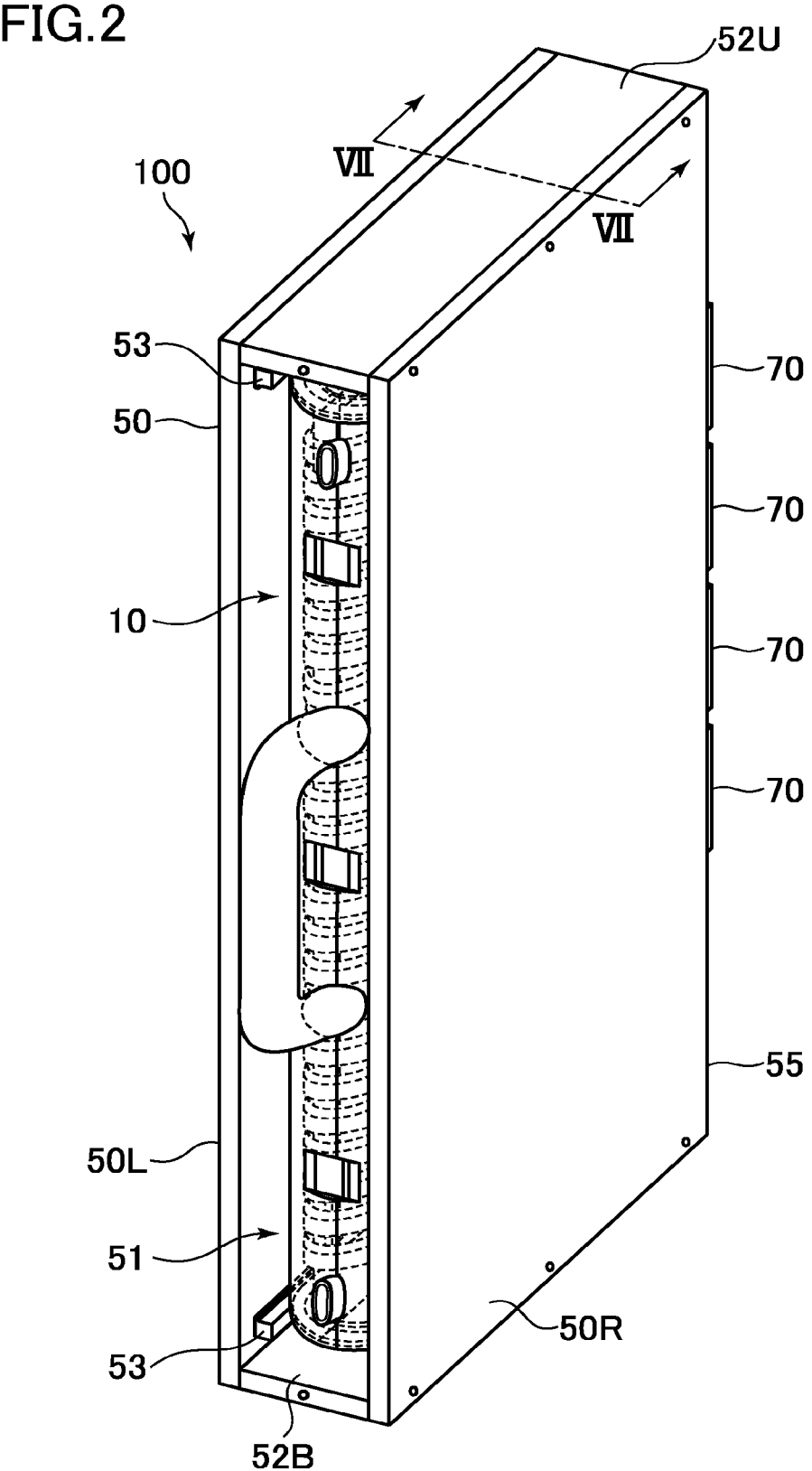
FIG. 2 is an outside perspective view for illustrating a photodynamic therapy device according to the embodiment.

FIG. 2 is an outside perspective view for illustrating the photodynamic therapy device 100 according to this embodiment. As illustrated in FIG. 2, the photodynamic therapy device 100 according to this embodiment includes a cartridge 10 and a casing 50 configured to accommodate the cartridge 10. The photodynamic therapy device 100 also includes other devices (not shown) such as a power supply device, a controller, and a blood circulation pump. The casing 50 has a thin box-like shape, and includes a left side plate 50L and a right side plate 50R. The left side plate 50L and the right side plate 50R each have a light-emitting portion including LED light sources on its inner surface, and are arranged on the left and the right so as to be opposed to each other. An upper part of the casing 50 is covered with an upper plate 52U, and a lower part thereof is covered with a bottom plate 52B. Further, a back side of the casing 50 is covered with a back plate 55. A plurality of fans 70 are provided on the back plate 55, and are configured to forcibly exhaust heat generated from the light-emitting portions described above to an outside. Further, an opening 51 on a front side is closed by a lid (not shown) so as to prevent light leakage. The lid may have an air inlet port.

Figure 3:
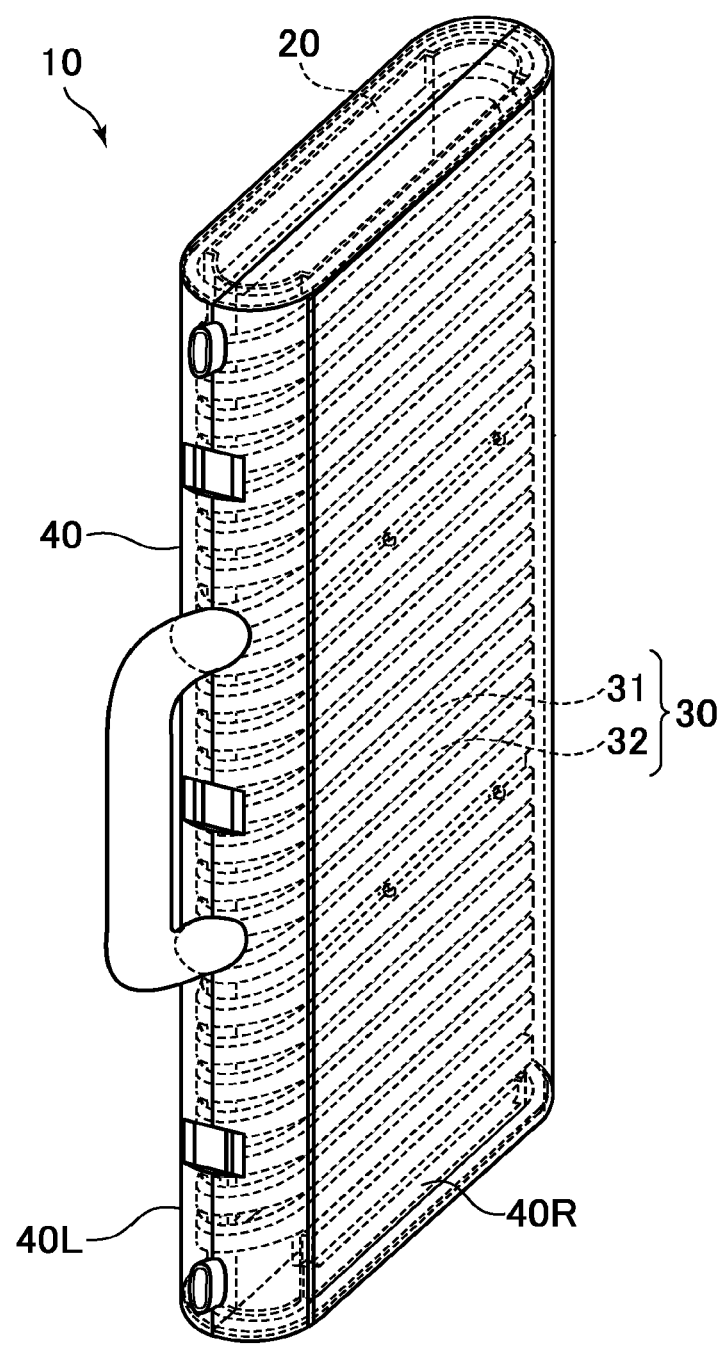
FIG. 3 is an outside perspective view for illustrating a cartridge according to the embodiment.
Figure 4:
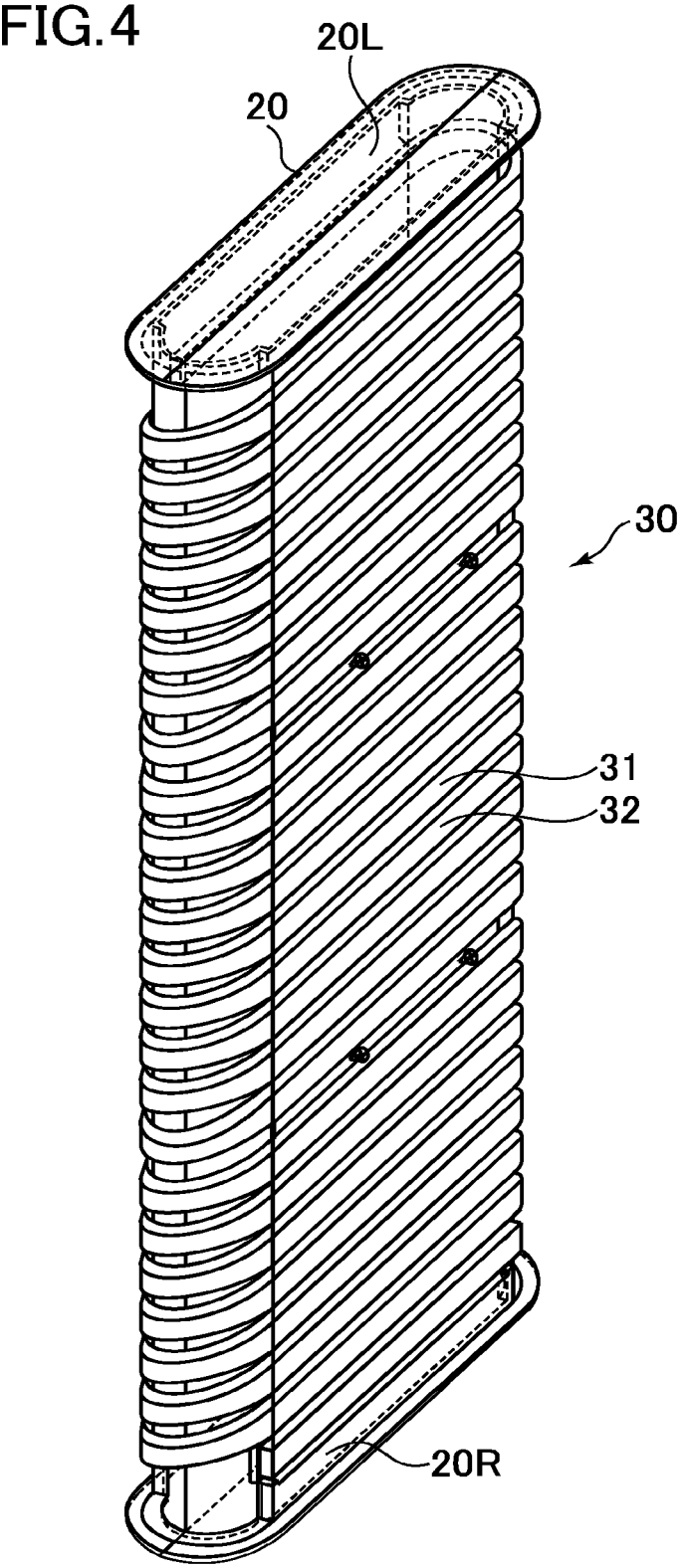
FIG. 4 is a perspective view for illustrating an internal structure of the cartridge according to the embodiment.
Figure 5:
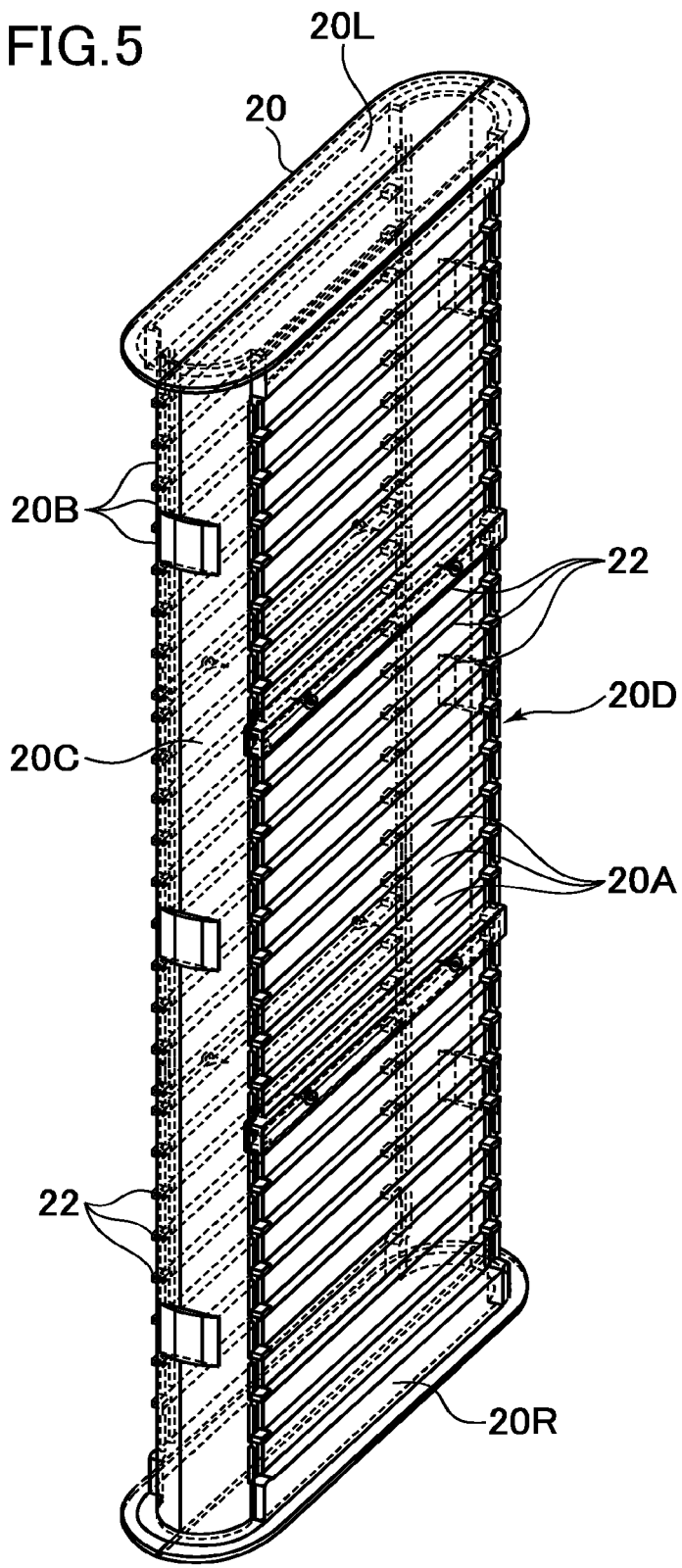
FIG. 5 is a perspective view for illustrating a winding core according to the embodiment.

FIG. 3 is an outside perspective view of the cartridge 10. FIG. 4 is a perspective view for illustrating an internal structure of the cartridge 10. FIG. 5 is a perspective view for illustrating a winding core 20 included in the cartridge 10. As illustrated in FIG. 3, the cartridge 10 is entirely covered with a cover 40, and has a thin box-like shape in such a size as to be accommodatable in the casing 50 as a whole. In particular, the cover 40 includes a left cover part 40L and a right cover part 40R, which are arranged on the left and the right so as to be opposed to each other. Each of the left cover part 40L and the right cover part 40R has a substantially flat plate-like shape with curved front and rear ends. A handle is provided at a front end of the cover 40. In FIG. 4, the cartridge 10 without the cover 40 is illustrated. The cartridge 10 includes the winding core 20 and a tube 30. The tube 30 is arranged so as to be wound around the winding core 20. The winding core 20 has an appearance illustrated in FIG. 5. The winding core 20 includes a left side plate 20L and a right side plate 20R, each being a structure body having a flat surface. The left side plate 20L and the right side plate 20R are provided on the left and the right so that their flat surfaces are opposed to each other. Each of front ends and rear ends of the left side plate 20L and the right side plate 20R has a curved wall portion. The left side plate 20L and the right side plate 20R are arranged so that the walls are smoothly connected to each other. The winding core 20 has an oval shape, that is, a shape obtained by connecting two opposed semicircles with parallel straight lines, or a rectangular shape with four rounded corners as an outer shape of a cross section taken along a horizontal direction. The tube 30 has a sufficient length to make a required number of turns (twenty-four turns in this case) around the winding core 20. As illustrated in FIG. 4, the tube 30 is wound around the winding core 20 without crossing or overlapping in the middle. In particular, a plurality of portions (for example, first portions 31 and second portions 32 illustrated in FIG. 4) of the tube 30, which are located on the flat surfaces of the left side plate 20L and the right side plate 20R, linearly extend, and are arranged in parallel to each other. The plurality of portions of the tube 30, which are located on the flat surfaces, extend in the horizontal direction in this embodiment. However, as a matter of course, the plurality of portions of the tube 30 may extend in a diagonal direction. The tube 30 has one end attached to the blood circulation pump and another end attached to a patient. Guide rails 53 are provided at an upper end and a lower end of an inner surface of each of the left side plate 50L and the right side plate 50R of the casing 50. The cartridge 10 is guided by the guide rails 53 so as to be insertable into and removable from the casing 50, and is single use for each patient.

Figure 6:
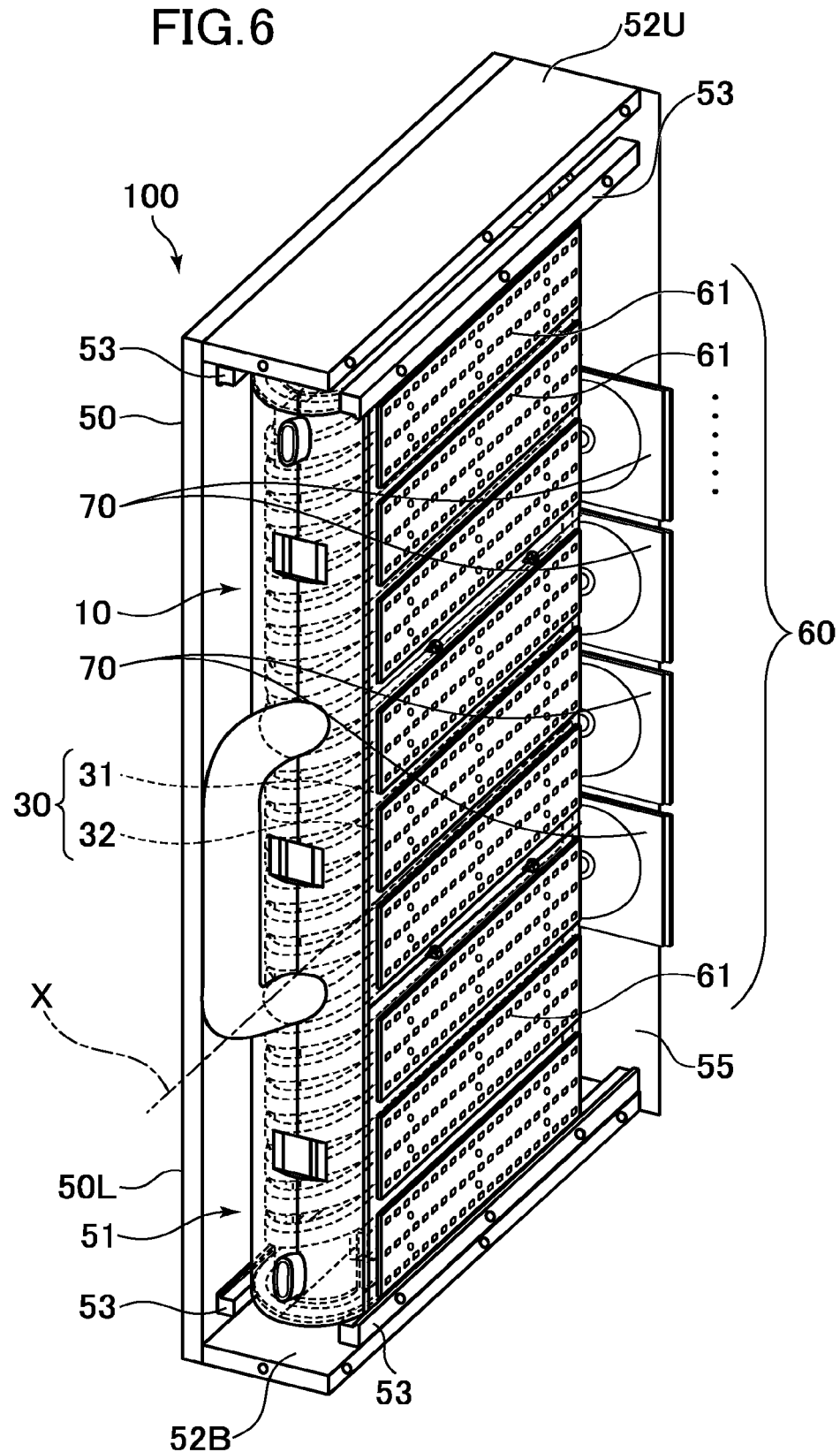
FIG. 6 is a perspective view for illustrating an internal structure of the photodynamic therapy device according to the embodiment.

FIG. 6 is a perspective view for illustrating an internal structure of the photodynamic therapy device 100 according to this embodiment. For illustration of the internal structure of the photodynamic therapy device 100, the right side plate 50R is removed from the photodynamic therapy device 100 illustrated in FIG. 6. As is understood by referring to FIG. and FIG. 4, a light source 60 is arranged on the inner surface of the right side plate 50R of the casing 50 so as to be opposed to the right side plate 20R of the cartridge 10, and radiate light to the tube 30 from its right side. A light source 60 is also arranged on the inner surface of the left side plate 50L of the casing 50 so as to be opposed to the left side plate 20L of the cartridge 10, and radiate light to the tube 30 from its left side (see FIG. 7). As an example, each of the light sources 60 includes a plurality of light-emitting elements 61 such as LED elements, which are arranged in, for example, matrix on a substrate. Blood of the patient flows through the tube 30. The blood has absorbed the photosensitive substance. Light irradiation from the light sources 60 produces singlet oxygen as described above, which can destroy or affect an undesirable component in the blood.

Figure 7:
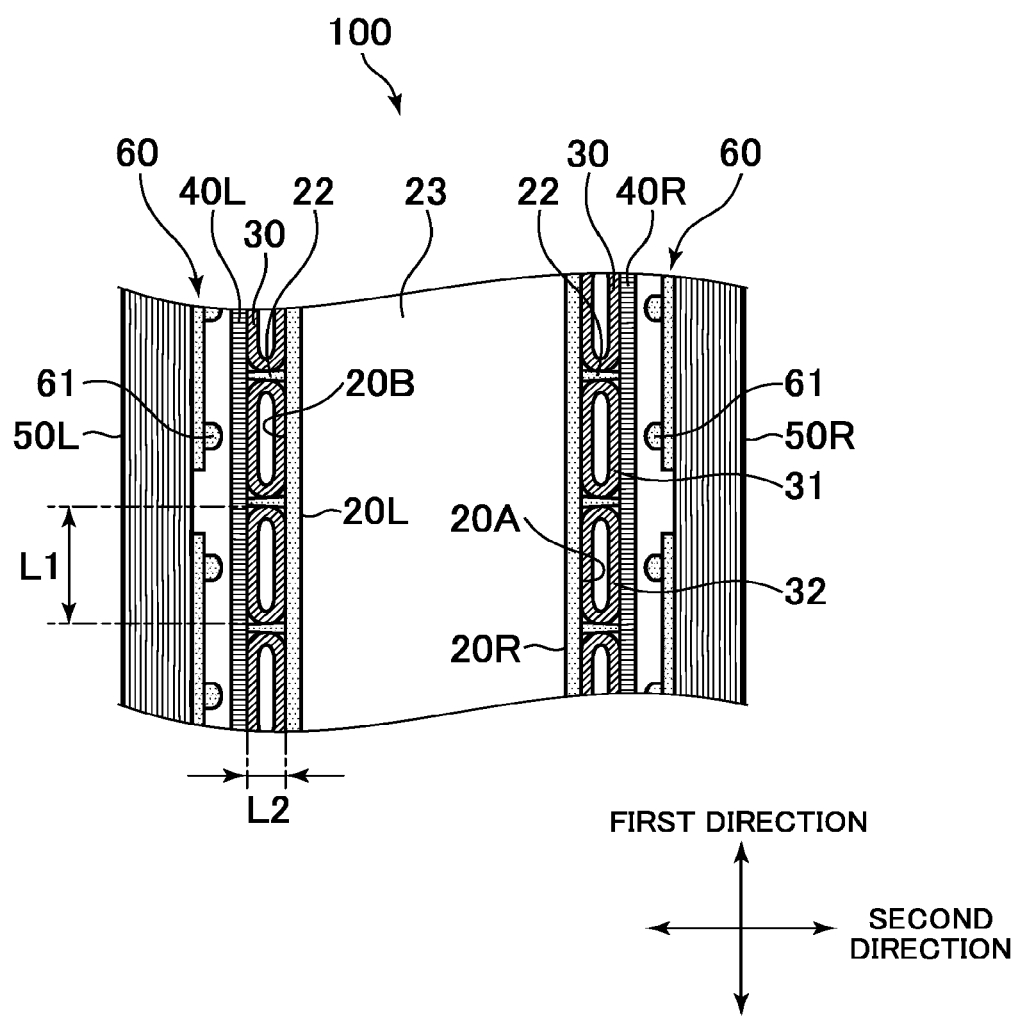
FIG. 7 is a partial sectional view taken along the line VII-VII of FIG. 2.

FIG. 7 is a partial sectional view taken along the line VII-VII of FIG. 2. A cross section of the tube 30, which is taken along a direction orthogonal to an extending direction of the tube 30, is illustrated in FIG. 7. The cross section of the tube 30, which is taken along the direction orthogonal to the extending direction of the tube 30, has a first dimension L1 and a second dimension L2. The first dimension L1 is a dimension in a first direction parallel to side surfaces of the winding core 20. The second dimension L2 is a dimension in a second direction orthogonal to the first direction. The second direction is an outward direction with respect to the winding core 20, that is, a direction in which the light sources 60 are arranged so as to be opposed to each other. The first dimension L1 corresponds to a maximum length in the first direction, and the second dimension L2 corresponds to a maximum length in the second direction. In this case, the second dimension L2 is smaller than the first dimension L1. A tube having an oval ring-like sectional shape may be used as the tube 30 so that an outer sectional shape of the tube 30 has the above-mentioned dimensions as a single body (by itself). An ellipsoid, a shape obtained by connecting two opposed semicircles with parallel straight lines, or a rectangular shape having four rounded corners may be used as the oval shape. Further, a square tube having a rectangular ring-like sectional shape may be used. Alternatively, the tube 30 having the outer sectional shape with the above-mentioned dimensions may be achieved in the following manner. A round tube is used as the tube 30, and an outer surface of the tube 30 is pressed inward with the cover 40. As a result, the above-mentioned dimensions are achieved under a state in which the tube 30 is mounted to the cartridge 10. When the tube itself has the outer sectional shape with the dimensions described above, the cover 40 is not indispensable.

The above-mentioned arrangement and dimensions enable an increase in projection area of the tube 30 onto each of the surfaces (light-emitting surfaces) on which the light sources 60 are provided. Thus, the blood flowing through the tube 30 can be efficiently irradiated with light from the light sources 60.

As illustrated in FIG. 7, a part of an inner surface of the cover 40, which is in contact with the tube 30, is formed flat. Thus, a shape of the tube 30 on the light source 60 side can be maintained flat. Further, the tube 30 is arranged so as to be in contact with flat surface portions 20A and flat surface portions 20B. Thus, a shape of the tube 30 on a side opposite to the light source 60 can also be maintained flat.

Now, a structure of the winding core 20 is described in further detail. As illustrated in FIG. 5, the winding core 20 is formed by fitting the left side plate 20L and the right side plate 20R, which are two left and right structure bodies, together. The winding core 20 has a columnar shape as a whole, which has a hollow cavity portion 23 (see FIG. 7) passing in a vertical direction. The right side plate 20R of the winding core 20 has the number of flat surface portions 20A, which corresponds to the number of turns of the tube 30. Similarly, the left side plate 20L of the winding core 20 has the same number of flat surface portions 20B as the number of flat surface portions 20A. All the flat surface portions 20A are defined on a first flat surface, and similarly, all the flat surface portions 20B are defined on a second flat surface. The first flat surface and the second flat surface are parallel to each other. The left side plate 20L and the right side plate 20R are provided so that the second flat surface is positioned at such a location that the first flat surface is moved in a direction normal to the first flat surface. The flat surface portions 20A are arranged to linearly extend along the first flat surface so as to be spaced apart from each other and parallel to each other. The flat surface portions 20B are also arranged to linearly extend along the second flat surface so as to be spaced apart from each other and parallel to each other. Guide walls 22 are provided upright between the flat surface portions 20A, and guide walls 22 are also provided upright between the flat surface portions 20B. Front ends of the flat surface portions 20A and front ends of the flat surface portions 20B are connected to each other through intermediation of a curved surface portion 20C, and rear ends of the flat surface portions 20A and rear ends of the flat surface portions 20B are connected to each other through intermediation of a curved surface portion 20D.

Portions (for example, the first portions 31 and the second portions 32) of the tube 30 are fitted into spaces defined by the flat surface portions 20A and the guide walls 22, 22 provided upright so as to be vertically adjacent to each of the flat surface portions 20A and spaces defined by the flat surface portions 20B and the guide walls 22 provided upright so as to be vertically adjacent to each of the flat surface portions 20B. The tube 30 is provided so as to be wound around the winding core 20 as a whole. As described above, the winding core 20 is covered with the cover 40. The tube 30 is arranged in a space surrounded by the flat surface portions 20A, the flat surface portions 20B, the guide walls 22, 22 provided upright so as to be vertically adjacent to each of the flat surface portions 20A and 20B, and the cover 40. In this case, a side surface of the tube 30 may be at least partially in contact with the inner surface of the cover 40. Further, a side surface of the tube 30 may be at least partially in contact with the flat surface portions 20A and the flat surface portions 20B. The flat surface portions 20A and the flat surface portions 20B extend in the horizontal direction in this embodiment. However, as a matter of course, the flat surface portions 20A and 20B may extend in the diagonal direction.

As illustrated in FIG. 7, a distance between each of the flat surface portions 20A and the right side plate 50R and a distance between each of the flat surface portions 20B and the left side plate 50L are equal to each other. The distances described above enable equalization of the amount of light to be radiated to the portions of the tube 30. Further, the distances described above can prevent the tube 30 and the light sources 60 from being located excessively close to each other to thereby prevent a temperature rise in the blood.

Now, a cooling structure of the photodynamic therapy device 100 is described. As illustrated in FIG. 6, the cooling fans 70 are arranged on the back plate 55 of the casing 50. As illustrated in FIG. 7, when viewed from the opening 51 side, clearances are defined between the inner surface of the left side plate 50L and a left side surface of the cartridge 10 and between the right side plate 50R and the cartridge 10, respectively. The clearances facilitate flow of air between the inner side surfaces of the casing 50 and the cartridge 10.

Further, as illustrated in FIG. 4 and FIG. 5, the portions (for example, the first portions 31 and the second portions 32) of the tube 30, which are located on the flat surface portions 20A of the winding core 20, linearly extend in parallel to each other. An extending direction of the linear portions of the tube 30 corresponds to, preferably, matches a direction of a straight line X, which is a direction of installation of the cooling fans 70 (axial direction of each of the fans). This arrangement allows air to more smoothly flow from the opening 51 toward the cooling fans 70 and from the cooling fans 70 toward the opening 51.

The smoothening of the flow of air caused by the cooling fans 70 can suppress a temperature rise in the cartridge 10. Further, when, for example, LED elements are used as the light-emitting elements 61 of the light sources 60, a center wavelength of emitted light may change due to a change in temperature of the LEDs. Such a change in center wavelength can be suppressed.

As described above, the winding core 20 has the hollow cavity portion 23 passing in the vertical direction. The hollow cavity portion 23 also enables promotion of heat rejection from the cartridge 10.

At least a part of the flat surface portions 20A and the flat surface portions 20B of the winding core 20 may be mirror finished. In this manner, light emitted from the light sources 60, which has transmitted through the tube 30, is reflected by the mirror finished part to be incident on the tube 30 again. Thus, the blood can be more efficiently irradiated with the light.

FIG. 8 is a sectional view for illustrating a photodynamic therapy device 100 according to a modification example. In this modification example, the left side plate 20L includes an additional flat surface portion 25 located between the flat surface portions 20B. The additional flat surface portion 25 may be defined on the same flat surface as the flat surface on which the flat surface portions 20B are defined. Similarly, the right side plate 20R includes an additional flat surface portion 25 located between the flat surface portions 20A. The additional flat surface portion 25 of the right side plate 20R may also be defined on the same flat surface as the flat surface on which the flat surface portions 20A are defined. The tube 30 is arranged so as not to be in contact with the additional flat surface portions 25.

In this case, when viewed in a direction normal to the flat surface portions 20B, that is, in the second direction illustrated in FIG. 8, the flat surface portion 20B and the additional flat surface portion 25 of the right side plate 20R may at least partially overlap with each other. Similarly, when viewed in the second direction, the flat surface portion 20A and the additional flat surface portion 25 of the left side plate 20L may at least partially overlap with each other. In this case, each of the left side plate 20L and the right side plate 20R is formed of a light-transmissive member. Alternatively, only the additional flat surface portions 25, the flat surface portions 20A, and the flat surface portions 20B may be formed of a light-transmissive member. For example, it is preferred that a member having a transmittance of 50° or higher to a center wavelength of the light emitted from the light sources 60 be used as the light-transmissive member. Alternatively, an opening may be formed in at least one of the additional flat surface portions 25, the flat surface portions 20A, or the flat surface portions 20B so as to allow the light emitted from the light sources 60 to more efficiently reach a back surface side. In the manner described above, the light emitted from the light sources 60 passes through portions between parallelly arranged portions of the tube 30 to be radiated onto the tube 30 on the back surface side.

The photodynamic therapy device 100 described above enables efficient irradiation of the blood of the patient with the light. The specific configuration disclosed herein is merely an example, and is not intended to limit the technical scope of the present invention thereto. Those skilled in the art may suitably modify the disclosed embodiment, and the technical scope of the invention according to this disclosure should be read as encompassing the thus made modifications.

A temperature control element such as a Peltier element may be arranged on a back surface of each of the light sources 60, and a thermometer may be arranged in the vicinity of each of the light sources 60 so that an operation of the temperature control element is controlled to keep a temperature of the light source 60 constant. Specifically, when the temperature of the light source 60 is higher than a reference value, the light source 60 is cooled by the temperature control element. When the temperature of the light source 60 is lower than the reference value, the light source 60 is heated by the temperature control element. In this manner, the temperature of each of the light sources 60 is kept constant. Each of the light-emitting elements 61 included in the light sources 60, such as LED elements, has a property of changing its wavelength depending on its temperature. Thus, the wavelength of light to be radiated to the blood can be kept constant by keeping the temperature constant.

APPENDICES

This disclosure encompasses the following configurations.

(1) A photodynamic therapy device, including:
a cartridge including:
a winding core; and
a tube arranged so as to be wound around the winding core;
a casing configured to accommodate the cartridge;
a light source, which is arranged inside the casing, and is configured to irradiate the tube with light,
wherein the winding core holds the tube so that a part of the tube extends along a first flat surface, and
wherein the light source includes a plurality of light-emitting elements arranged on a flat surface opposed to the first flat surface.

(2) A photodynamic therapy device cartridge, including:
a winding core; and
a tube arranged so as to be wound around the winding core,
wherein the winding core holds the tube so that a part of the tube extends along a first flat surface.

With the configurations (1) and (2) described above, an optical path length from the light source 60 to the tube 30 arranged on the first flat surface portions 20A can easily be set constant. Thus, the amount of light radiated to the blood flowing through the tube 30 can be made constant. As a result, a light absorption amount by the photosensitive substance can be kept constant. Hence, a given or higher effect of destroying or affecting an undesirable component in the blood can be ensured.

The tube 30 and the plurality of light-emitting elements 61 can be prevented from being located excessively close to each other by keeping a constant distance between the tube 30 and the plurality of light-emitting elements 61. As a result, a local temperature rise in the blood flowing through the tube can be suppressed. As a matter of course, the above-mentioned effects can be obtained regardless of a relationship between the dimension L1 and the dimension L2 of the tube 30.

REFERENCE SIGNS LIST

4 patient, 5 tumor cell, 6 blood circuit, 7 irradiation blood circuit, 8 extracorporeal circulation pump, 10 cartridge, 20 winding core, 22 guide wall, 23 hollow cavity portion, 30 tube, 40 cover, 50 casing, 60 light source, 70 cooling fan, 100 photodynamic therapy device, L1 first dimension, L2 second dimension.

The invention claimed is:

1. A photodynamic therapy device, comprising:
a cartridge including:
a winding core; and
a tube arranged so as to be wound around the winding core;
a casing configured to accommodate the cartridge; and
a light source, which is arranged inside the casing, and is configured to irradiate the tube with light,
wherein the tube arranged around the winding core has a cross section taken along a direction orthogonal to an extending direction of the tube, which has a first dimension in a first direction and a second dimension in a second direction orthogonal to the first direction, the second dimension being smaller than the first dimension, and the second direction is directed outward with respect to the winding core.

2. The photodynamic therapy device according to claim 1, wherein the winding core holds the tube so that a part of the tube extends along a first flat surface.

3. The photodynamic therapy device according to claim 2, wherein the tube has a first portion and a second portion extending in parallel along the first flat surface.

4. The photodynamic therapy device according to claim 3, wherein the tube is arranged so that the first portion and the second portion are spaced apart from each other,
wherein the tube further includes a third portion extending along a second flat surface located on a back side of the first flat surface,
wherein at least a part of the third portion is located between the first portion and the second portion when viewed in a direction orthogonal to the first flat surface, and
wherein a portion of the winding core, which is located on a side closer to the first flat surface with respect to the third portion, is formed of a light-transmissive member.

5. The photodynamic therapy device according to claim 4, wherein the light-transmissive member has a light transmittance of 50% or higher to a center wavelength of the light emitted from the light source.

6. The photodynamic therapy device according to claim 3, further comprising a cooling fan arranged on the casing,
wherein the first portion and the second portion linearly extend in accordance with a direction of installation of the cooling fan.

7. The photodynamic therapy device according to claim 6, wherein the casing and the cartridge are arranged so as to define clearances between inner side surfaces of the casing and side surfaces of the cartridge, respectively.

8. The photodynamic therapy device according to claim 2, wherein the light source includes a plurality of light-emitting elements arranged on a flat surface opposed to the first flat surface.

9. The photodynamic therapy device according to claim 8, wherein the casing and the cartridge are arranged so as to define clearances between inner side surfaces of the casing and side surfaces of the cartridge, respectively.

10. The photodynamic therapy device according to claim 1, wherein at least a part of the winding core, with which the tube is arranged in contact, is mirror finished.

11. The photodynamic therapy device according to claim 1, further comprising a cover configured to hold the tube in cooperation with the winding core,
wherein a part of the cover, which is in contact with the tube, has a flat surface.

12. The photodynamic therapy device according to claim 1, wherein the winding core has a tubular shape, and has a hollow cavity portion passing from one end to another end of the tubular shape.

13. A photodynamic therapy device cartridge, comprising:
a winding core; and
a tube arranged so as to be wound around the winding core,
wherein the tube arranged around the winding core has a cross section taken along a direction orthogonal to an extending direction of the tube, which has a first dimension in a first direction and a second dimension in a second direction orthogonal to the first direction, the second dimension being smaller than the first dimension, and the second direction is directed outward with respect to the winding core.

14. The photodynamic therapy device cartridge according to claim 13, wherein the winding core holds the tube so that a part of the tube extends along a first flat surface.

15. The photodynamic therapy device cartridge according to claim 14, wherein the tube has a first portion and a second portion extending in parallel along the first flat surface.

16. The photodynamic therapy device cartridge according to claim 15,
wherein the tube is arranged so that the first portion and the second portion are spaced apart from each other,
wherein the tube further includes a third portion extending along a second flat surface located on a back side of the first flat surface,
wherein at least a part of the third portion is located between the first portion and the second portion when viewed in a direction orthogonal to the first flat surface, and
wherein a portion of the winding core, which is located on a side closer to the first flat surface with respect to the third portion, is formed of a light-transmissive member.

17. The photodynamic therapy device cartridge according to claim 16, wherein the light-transmissive member has a light transmittance of 50% or higher with respect to a center wavelength of light to be radiated to the tube.

18. The photodynamic therapy device cartridge according to claim 13, wherein at least a part of the winding core, with which the tube is arranged in contact, is mirror finished.

19. The photodynamic therapy device cartridge according to claim 13, further comprising a cover configured to hold the tube in cooperation with the winding core,
wherein a part of the cover, which is in contact with the tube, has a flat surface.

20. The photodynamic therapy device cartridge according to claim 13, wherein the winding core has a tubular shape, and has a hollow cavity portion passing from one end to another end of the tubular shape.

* * * * *